(12) United States Patent
Radhakrishnan et al.

(10) Patent No.: US 10,262,108 B2
(45) Date of Patent: Apr. 16, 2019

(54) SYSTEM AND METHOD FOR DETERMINING TRIAGE CATEGORIES

(71) Applicant: Board of Regents of the University of Texas System, Austin, TX (US)

(72) Inventors: Hari Radhakrishnan, Houston, TX (US); Michelle Scerbo, Houston, TX (US); John B. Holcomb, Bellaire, TX (US); Charles E. Wade, Houston, TX (US)

(73) Assignee: BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 764 days.

(21) Appl. No.: 14/773,101

(22) PCT Filed: Mar. 3, 2014

(86) PCT No.: PCT/US2014/019878
§ 371 (c)(1),
(2) Date: Sep. 4, 2015

(87) PCT Pub. No.: WO2014/137892
PCT Pub. Date: Sep. 12, 2014

(65) Prior Publication Data
US 2016/0012192 A1    Jan. 14, 2016

Related U.S. Application Data

(60) Provisional application No. 61/772,172, filed on Mar. 4, 2013.

(51) Int. Cl.
*G06F 19/00* (2018.01)
*G16H 10/60* (2018.01)
*G16H 50/20* (2018.01)

(52) U.S. Cl.
CPC .......... *G06F 19/3418* (2013.01); *G06F 19/00* (2013.01); *G16H 10/60* (2018.01); *G16H 50/20* (2018.01)

(58) Field of Classification Search
CPC .. G06F 19/322; G06F 19/345; G06F 19/3418; G06F 15/18; G16H 10/60;
(Continued)

(56) References Cited

U.S. PATENT DOCUMENTS 7,895,137 B2    2/2011  Salahshour et al.
7,925,603 B1 *  4/2011  Laidig .................... G06Q 10/04
                                                706/45
(Continued)

FOREIGN PATENT DOCUMENTS

WO    WO2011115576 A2    9/2011

OTHER PUBLICATIONS

Pollettini J. et al., "Using Machine Learning Classifiers to Assist Healthcare-Related Decisions: Classification of Electronic Patient Records", J Med Syst, 2012.*
(Continued)

*Primary Examiner* — Dave Misir
(74) *Attorney, Agent, or Firm* — Sprinkle IP Law Group

(57) ABSTRACT

Embodiments disclosed herein provide a system, method, and computer program product for providing a triage classification system. The triage classification system uses a computer model that is developed using historical patient data. The developed computer model is applied to collected patient attribute data from a patient in a pre-hospital setting to generate a triage category. Based on the generated triage category, health care professionals can take desired actions, such as transporting the patient to a facility matching the generated triage category.

20 Claims, 3 Drawing Sheets

(58) Field of Classification Search
CPC ........ G16H 50/20; G16H 50/30; G16H 40/20; G06Q 10/06; G06Q 50/22; G06N 99/005
USPC .......................................................... 706/12
See application file for complete search history.

(56) References Cited

U.S. PATENT DOCUMENTS

| | | | |
|---|---|---|---|
| 8,055,596 B2 | 11/2011 | Bhaskar et al. | |
| 8,244,652 B2 | 8/2012 | Menahem et al. | |
| 8,832,558 B2 | 9/2014 | Cardarelli et al. | |
| 2005/0285385 A1* | 12/2005 | Bova | B42D 15/00 283/75 |
| 2006/0271407 A1* | 11/2006 | Rosenfeld | A61B 5/412 705/3 |
| 2007/0226008 A1* | 9/2007 | Halsted | G06Q 10/10 705/2 |
| 2009/0177599 A1* | 7/2009 | Bhaskar | G06N 3/126 706/13 |
| 2009/0182696 A1* | 7/2009 | Menahem | G06K 9/6292 706/20 |
| 2009/0276383 A1* | 11/2009 | Salahshour | G06F 9/542 706/12 |
| 2011/0054946 A1* | 3/2011 | Coulter | G06Q 10/06 705/3 |
| 2011/0301965 A1* | 12/2011 | Hitney | G06Q 50/22 705/2 |
| 2015/0150514 A1* | 6/2015 | Batchinsky | A61B 5/7275 600/301 |

OTHER PUBLICATIONS

Extended European Search Report issued for European Patent Application No. 14 761 262.6, dated Oct. 16, 2016, 9 pages.
International Search Report and Written Opinion issued for PCT Application No. PCT/US2014/019878, dated Jun. 3, 2014, 7 pages.
International Preliminary Report on Patentability (IPRP) issued for PCT Application No. PCT/US2014/019878, dated Mar. 9, 2015, 14 pages.
Office Action for European Patent Application No. 14761262.6, dated Nov. 20, 2018, 9 pgs.
Anonymous: "Training, validation, and tests sets," Wikipedia, Dec. 11, 2012, XP055523278, retrieved from the Internet on Nov. 13, 2018 at URL:https://en.wikipedia.org/w/index.ph?Title=Training_validation,_and_test_sets@oldid=527492310, 1 pg.

* cited by examiner

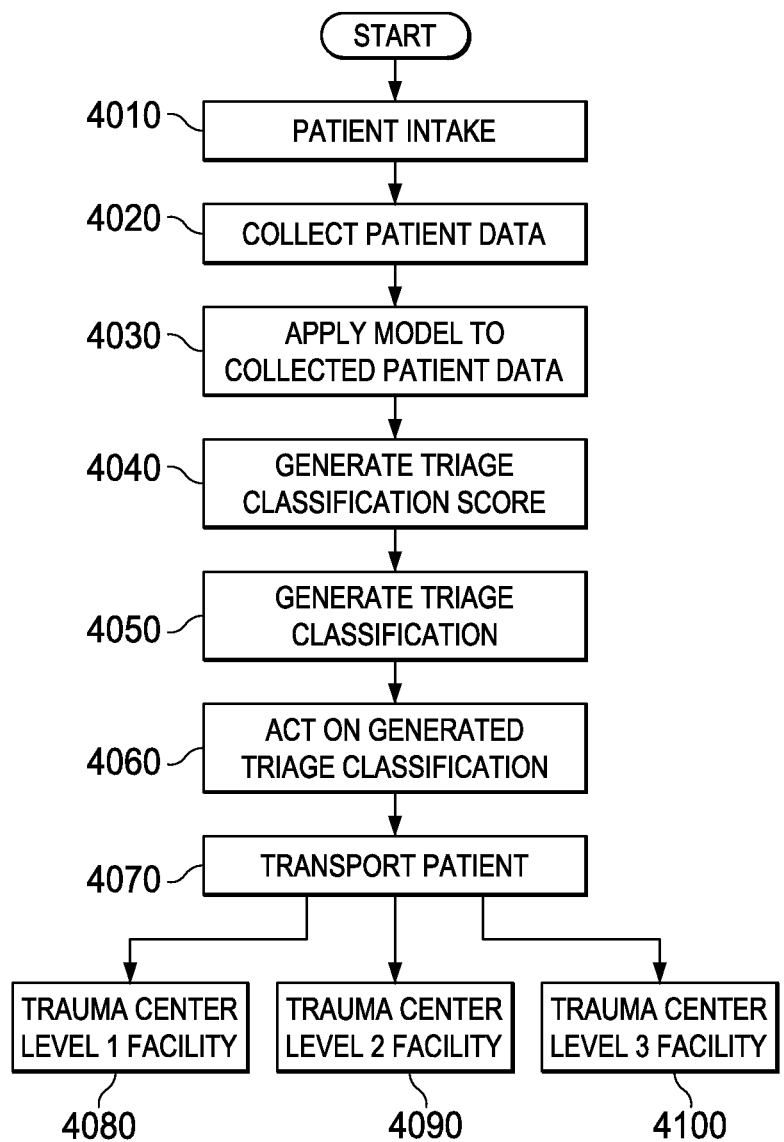

SYSTEM AND METHOD FOR DETERMINING TRIAGE CATEGORIES

CROSS-REFERENCE TO RELATED APPLICATION(S)

This is a national stage application of International Application No. PCT/US2014/019878, filed Mar. 3, 2014 entitled "SYSTEM AND METHOD FOR DETERMINING TRIAGE CATEGORIES," and claims a benefit of priority from U.S. Provisional Application No. 61/772,172, filed Mar. 4, 2013, entitled "SYSTEM AND METHOD FOR DETERMINING TRIAGE CATEGORIES." This application relates to International Application No. PCT/US2014/023329, filed Mar. 11, 2014, entitled "SYSTEM AND METHOD FOR A PATIENT DASHBOARD," which claims a benefit of priority from U.S. Provisional Application No. 61/780,174, filed Mar. 13, 2013, entitled "SYSTEM AND METHOD FOR A PATIENT DASHBOARD." All applications listed in this paragraph are incorporated by reference as if set forth herein in their entireties.

TECHNICAL FIELD

This disclosure relates generally to the field of medical informatics. More specifically, the disclosure relates to the computerized determination of triage categories for patients. Even more particularly, the disclosure relates to computerized assistance in the assignment of a triage category to a patient in a pre-hospital setting.

BACKGROUND OF THE RELATED ART

Typically, a particular community or geographical area has a limited number of trauma centers. These trauma centers are usually segmented into levels, with the highest level trauma centers, that are capable of providing comprehensive service to treat traumatic injuries, being assigned a Level 1 designation while more limited care facilities being assigned a Level 2 or 3 designation. Thus, trauma victims may be triaged (e.g., assigned a trauma category, which may correspond with a level designation for a trauma center) based on a set of criteria. The patient can then be transported or otherwise delivered into the care of a trauma center with a level corresponding to the assigned category.

Trauma Center designation is a process outlined and developed at a state or local level. The state or local municipality identifies unique criteria in which to categorize Trauma Centers. These categories may vary from state to state and are typically outlined through legislative or regulatory authority. Following are exemplary definitions of various trauma center levels, as defined by the American Trauma Society (ATS). Other definitions are also possible.

A Level I Trauma Center is a comprehensive regional resource that is a tertiary care facility central to the trauma system. A Level I Trauma Center is capable of providing total care for every aspect of injury—from prevention through rehabilitation. Elements of Level I Trauma Centers Include:

24-hour in-house coverage by general surgeons, and prompt availability of care in specialties such as orthopedic surgery, neurosurgery, anesthesiology, emergency medicine, radiology, internal medicine, plastic surgery, oral and maxillofacial, pediatric and critical care.

Referral resource for communities in nearby regions.

Provides leadership in prevention, public education to surrounding communities.

Provides continuing education of the trauma team members.

Incorporates a comprehensive quality assessment program.

Operates an organized teaching and research effort to help direct new innovations in trauma care.

Program for substance abuse screening and patient intervention.

Meets minimum requirement for annual volume of severely injured patients.

A Level II Trauma Center is able to initiate definitive care for all injured patients. Elements of Level II Trauma Centers Include:

24-hour immediate coverage by general surgeons, as well as coverage by the specialties of orthopedic surgery, neurosurgery, anesthesiology, emergency medicine, radiology and critical care.

Tertiary care needs such as cardiac surgery, hemodialysis and microvascular surgery may be referred to a Level I Trauma Center.

Provides trauma prevention and to continuing education programs for staff.

Incorporates a comprehensive quality assessment program.

A Level III Trauma Center has demonstrated an ability to provide prompt assessment, resuscitation, surgery, intensive care and stabilization of injured patients and emergency operations. Elements of Level III Trauma Centers Include:

24-hour immediate coverage by emergency medicine physicians and the prompt availability of general surgeons and anesthesiologists.

Incorporates a comprehensive quality assessment program

Has developed transfer agreements for patients requiring more comprehensive care at a Level I or Level II Trauma Center.

Provides back-up care for rural and community hospitals.

Offers continued education of the nursing and allied health personnel or the trauma team.

Involved with prevention efforts and must have an active outreach program for its referring communities.

A Level IV Trauma Center has demonstrated an ability to provide advanced trauma life support (ATLS) prior to transfer of patients to a higher level trauma center. It provides evaluation, stabilization, and diagnostic capabilities for injured patients. Elements of Level IV Trauma Centers Include:

Basic emergency department facilities to implement ATLS protocols and 24-hour laboratory coverage.

Available trauma nurse(s) and physicians available upon patient arrival.

May provide surgery and critical-care services if available.

Has developed transfer agreements for patients requiring more comprehensive care at a Level I or Level II Trauma Center.

Incorporates a comprehensive quality assessment program

Involved with prevention efforts and must have an active outreach program for its referring communities.

A Level V Trauma Center provides initial evaluation, stabilization and diagnostic capabilities and prepares patients for transfer to higher levels of care. Elements of Level IV Trauma Centers Include:

Basic emergency department facilities to implement ATLS protocols

Available trauma nurse(s) and physicians available upon patient arrival.

After-hours activation protocols if facility is not open 24-hours a day.

May provide surgery and critical-care services if available.

Has developed transfer agreements for patients requiring more comprehensive care at a Level I though III Trauma Centers.

A facility can be designated an adult trauma center, a pediatric trauma center, or an adult and pediatric trauma center. If a hospital provides trauma care to both adult and pediatric patients, the Level designation may not be the same for each group. For example, a Level 1 adult trauma center may also be a Level 2 pediatric trauma center. This is because pediatric trauma surgery is a specialty unto itself.

Accurately triaging patients is difficult. In most cases, the triaging occurs in a pre-hospital setting such as when first responders or emergency medical service personnel are assessing or transporting the patient. Appropriate triage of trauma patients is vital for efficient utilization of trauma resources and the delivery of appropriate care. Under triage (assignment of a lower triage category to a patient that should be assigned a higher triage category) is extremely problematic, as the patient may not receive appropriate care. Over triage (assignment of a higher triage category to a patient that should be assigned a lower triage category) can also be problematic by forcing patients out of their community unnecessarily, wasting resources, and delaying treatment for those critically injured.

SUMMARY OF THE DISCLOSURE

Embodiments disclosed herein provide a system and method for determining triage categories for patients. In some embodiments, a computer model is developed using a training data set comprised of historical patient data. The computer model is applied to collected patient attribute data from a patient in a pre-hospital setting to generate a triage category.

Embodiments disclosed herein can provide many advantages. For example, over triage rates can be reduced while not significantly increasing under triage rates. The computer model can be tuned to achieve desired over triage and under triage rates. The computer model can also be trained using patient data from specific geographic regions.

BRIEF DESCRIPTION OF THE DRAWINGS

The drawings accompanying and forming part of this specification are included to depict certain aspects of the invention. A clearer impression of the invention, and of the components and operation of systems provided with the invention, will become more readily apparent by referring to the exemplary, and therefore nonlimiting, embodiments illustrated in the drawings, wherein identical reference numerals designate the same components. Note that the features illustrated in the drawings are not necessarily drawn to scale.

FIG. 4 is a flow chart depicting a process of applying a developed triage classification model to patient data.

DETAILED DESCRIPTION

Figure 1:
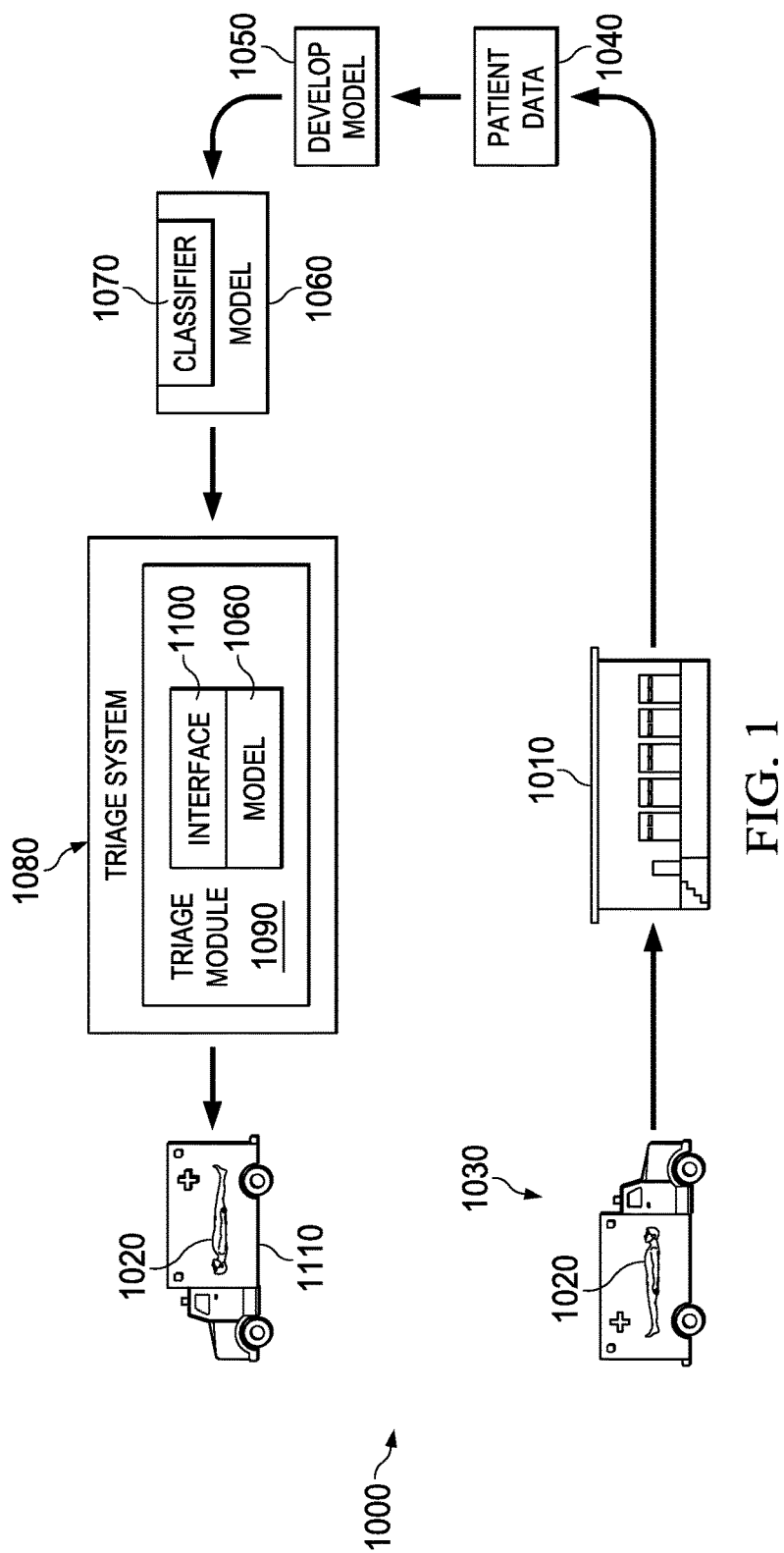
FIG. 1 is a block diagram of one embodiment of a topology of a triage system.

The invention and the various features and advantageous details thereof are explained more fully with reference to the nonlimiting embodiments that are illustrated in the accompanying drawings and detailed in the following description. Descriptions of well-known starting materials, processing techniques, components and equipment are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure. Embodiments discussed herein can be implemented in suitable computer-executable instructions that may reside on a computer readable medium (e.g., a HD), hardware circuitry or the like, or any combination.

Before discussing specific embodiments, embodiments of a hardware architecture for implementing certain embodiments is generally described herein and will be discussed in more detail later. One embodiment can include one or more computers communicatively coupled to a network. As is known to those skilled in the art, the computer can include a central processing unit ("CPU"), at least one read-only memory ("ROM"), at least one random access memory ("RAM"), at least one hard drive ("HD"), and one or more input/output ("I/O") device(s). The I/O devices can include a keyboard, monitor, printer, electronic pointing device (such as a mouse, trackball, stylus, etc.), or the like. In various embodiments, the computer has access to at least one database over the network.

ROM, RAM, and HD are tangible computer readable medium for storing computer-executable instructions executable by the CPU. Within this disclosure, the term "computer-readable medium" is not limited to ROM, RAM, and HD and can include any type of data storage medium that can be read by a processor. In some embodiments, a tangible computer-readable medium may refer to a data cartridge, a data backup magnetic tape, a floppy diskette, a flash memory drive, an optical data storage drive, a CD-ROM, ROM, RAM, HD, or the like.

At least portions of the functionalities or processes described herein can be implemented in suitable computer-executable instructions. The computer-executable instructions may be stored as software code components or modules on one or more computer readable media (such as non-volatile memories, volatile memories, DASD arrays, magnetic tapes, floppy diskettes, hard drives, optical storage devices, etc. or any other appropriate computer-readable medium or storage device). In one embodiment, the computer-executable instructions may include lines of complied C++, Java, HTML, or any other programming or scripting code.

Additionally, the functions of the disclosed embodiments may be implemented on one computer or shared/distributed among two or more computers in or across a network. Communications between computers implementing embodiments can be accomplished using any electronic, optical, radio frequency signals, or other suitable methods and tools of communication in compliance with known network protocols.

As used herein, the terms "comprises," "comprising," "includes," "including," "has," "having" or any other variation thereof, are intended to cover a non-exclusive inclusion. For example, a process, process, article, or apparatus that comprises a list of elements is not necessarily limited to only those elements but may include other elements not expressly listed or inherent to such process, process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," "in one embodiment."

A brief discussion of context, particularly with respect to trauma, may be helpful. According to recent Centers for Disease Control and Prevention (CDC) statistics, trauma accounts for more than 42 million emergency department visits and more than 2 million hospital admissions every year in the United States. As mentioned above, in most cases, a particular community or geographical area has a limited number of trauma centers (e.g., locations where trauma patients may be treated, such as hospitals or the like). These trauma centers are usually segmented into levels, with the highest level trauma centers, that are capable of providing comprehensive service to treat traumatic injuries, being assigned a Level 1 designation while more limited care facilities being assigned a Level 2 or 3 designation (or lower, as in some cases states may have their own ranking scale for such trauma centers) based on their capabilities. As patients come into a system, they may be triaged based on a set of criteria. The patients can then be transported or otherwise delivered into the care of a trauma center with a triage level corresponding to the assigned category.

The appropriate triage of trauma patients is vital for efficient utilization of trauma resources and the delivery of appropriate care. Under triage (assignment of a lower triage category to a patient that should be assigned a higher triage category and delivering the patient to a trauma center associated with the lower category) is extremely problematic, as the patient may not receive appropriate care. While such under triage can have devastating consequences, over triage (assigning a patient a higher triage category than the patient requires and delivering the patient to a higher level trauma center) can also be problematic by forcing patients out of their community unnecessarily, wasting resources and delaying, treatment for those critically injured. These problems may be especially critical in a mass emergency/casualty settings such as during severe weather accidents involving mass transit, terrorist attacks, etc. where it may especially important to distribute patients across trauma centers such that resources can be applied appropriately.

As mentioned above, accurately triaging patients is difficult. In most cases, the triaging (e.g., assignment of a trauma category) occurs in a pre-hospital setting, such as when first responders or emergency medical service personnel are assessing or transporting the patient. In many instances, to make such an assignment, a checklist may be used, where the checklist specifies values for one or more criteria (e.g., values for vital signs, location or type of trauma, etc.). The patient is assigned to a trauma category based on this checklist and on values for the one or more criteria associated with that patient.

There are a number of problems with current techniques of assigning trauma categories to patients. One problem stems from the variability of checklists across geographic regions and care providers. In some cases, this variability results in care providers, such as first responders or transport providers, using different checklists within the same locale (e.g., when the options for treatment for each of those patients is the same).

Furthermore, such checklists may be restricted to the use of only few criteria (e.g., for various reasons, such as complexity of determination of values for these criteria, time concerns in the applicability of such checklists, etc.) and thus, the granularity of assignment of triage categories may be rather large. For example, in most instances, there are only two types of these checklists, one to apply to adults and one to used assign triage levels to children. Additionally, trauma categories are assigned mainly based on three domains: physiology, mechanism of injury, and anatomical location of injury. These domains may be defined during an initial physical exam of the patient in a pre-hospital environment. In some instances, these three domains may be insufficient for accurate category assignment.

Moreover, as it may be desired to err on the side of caution, these checklists may be inherently constructed to bias the assignment of triage category to a patient to substantially eliminate instances of under triage. Of course, such a bias may result in over triage. In fact, in 1999 a generally accepted over triage rate of around 50% was established. While this over triage rate has been re-evaluated it has really never been broadly and effectively reduced. Consequently, it is desired to substantially reduce this over triage rate, while not substantially increasing (or increasing at all) the under triage rate.

Accordingly, attention is directed to the systems and methods for determining triage categories for patients depicted herein. Specifically, embodiments of such triage systems and methods may be employed in certain settings (e.g., pre-hospital) to more accurately assign a triage category to a patient based on multiple variables associated with a patient. Such systems may employ a model to provide a triage category recommendation based on data for the multiple variables obtained for the patient. In some examples, the model is created, tested and tuned based on patient data obtained from previously triaged patients. Thus, by using the model, a more accurate triage category may be assigned to a patient. Furthermore, a triage system may be developed based on data collected in a particular environment, resulting in a triage system tailored to that particular environment (e.g., the different triage levels present in a geographic region, etc.). In some examples, it has been determined that a triage system as depicted herein may reduce the over triage rate by approximately 24%, while substantially maintaining the under triage rate.

Embodiments of such systems and methods may be better understood with reference to FIG. 1, which depicts one embodiment of a topology in which a triage system may be developed and deployed. FIG. 1 depicts system 1000, including a trauma center 1010 (for example, a hospital) that accept patients 1020. The trauma center 1010 may have its own assigned triage level (e.g., level 1, level 2, etc.) and may accept patients that have been assigned a triage category in a pre-hospital setting 1030. Examples of pre-hospital settings in which a triage category is assigned include during transport to the trauma center 1010, at some other point by first responders, during patient intake at the trauma center 1010, etc. It should be understood that, while embodiments as described herein may be described in conjunction with their use in a pre-hospital environment, other embodiments may also be applied in other settings in which it is desired to assign a triage category to a patient.

When a patient is received at the trauma center 1010, patient data 1040 is collected and maintained. The patient data 1040 may be collected at the trauma center by elements within the trauma center (e.g., a research branch) or some other entity (e.g., a $3^{rd}$ party consultant or research group, etc.). The patient data 1040 may include the triage category the patient was assigned in the pre-hospital setting, vital signs determined at multiple points in the pre-hospital environment, patient demographics, mechanism of injury, interventions (e.g., pre-hospital fluid, medications), patient management characteristics, site of injury, disposition (e.g., the accuracy of the initial triage level assigned in the pre-hospital setting, a triage level to which the patient should have been assigned, for example, based on patient outcome or treatment, etc.), bleeding status, pulse character, or other attributes. As one skilled in the art would understand, there may be numerous attributes on which data is collected (e.g., on the order of 80 or more).

As shown in block 1050 of FIG. 1, the patient data 1040 collected from numerous patients may be used to develop a model for assigning a triage level to a patient. A model 1060 may be, for example, a statistical model that includes a classifier 1070. The classifier 1070 may be configured to take as input one or more values for attributes collected from a patient. Based on the values of those attributes, the model 1060 determines a triage category for the patient. In some embodiments, the classifier may be able to effectively treat the attributes as functionally continuous. The classifier can therefore catch subtle differences in values of the collected attributes that may result in difference in triage categorization even though actual differences of the values in the data set may not be large.

The classifier is able to deal with a large number of input variables and work with incomplete data (e.g., determine a triage level based on fewer attributes than were used to develop the classifier). In addition, some embodiments of classifiers may use multiple techniques to achieve a more accurate assignment of triage level relative to the use of simpler, or a single, technique.

Accordingly, in one embodiment, a classifier may be comprised of an ensemble classifier such as random forest, rotation forest, LogitBoost (e.g., additive logistic regression, random subspace alternating decision trees and learns alternating decision trees using LogitBoost). These types on ensemble classifiers are listed by way of example, and it should be understood that others may also be used. In some examples, the use of an ensemble classifier may work better than other classifiers that may be utilized (e.g., logistic regression, naive Bayesian analysis, multilayer perceptron), as these simpler techniques give poorer results when faced with a complex system. Ensemble classifiers use multiple techniques to achieve a more accurate classification, while simpler techniques such as Bayes and logistic regression may be limited to one type of analysis. Using multiple techniques allows for an increased size of data input parameters and often produces a statistically significant predictor when other, simpler techniques may not work as well.

In one embodiment, the classifier may be comprised of a random forest classifier algorithm for pre-hospital triage of patients. Such a classifier takes inputs (e.g., values for attributes, including, for example, vital signs) and determine an appropriate triage category. Such a random forest classifier may be an ensemble classifier that uses a combination of many decision trees with the number of votes from all (or a subset of votes from the decision trees) determining the appropriate level of triage. Each tree depends on the values of a random vector sampled independently and with the same distribution for all trees in the forest.

In some embodiments, after a model is developed, the classifier may be tuned according to a desired over triage rate or a desired under triage rate. The tuning of a classifier may be accomplished using cost sensitization, pruning or out of bag error such that the assignment of a triage level based on the classifier may be more likely to yield the desired under triage or over triage rate.

Referring again to FIG. 1, once the model 1060 has been developed, it may be deployed or otherwise utilized in a triage system 1080. A triage system 1080 may be employed in a pre-hospital setting. The triage system 1080 includes a triage module 1090 having an interface 1100 and the model 1060. The interface 1100 may accept inputs such as values for a variety of attributes. These inputs may be input manually (e.g., by a first responder or other operator of the triage system 1080) or may be obtained through the interface automatically (e.g., from various monitors or other devices, for example, using the HL7 protocol or the like).

Using the inputs received through the interface 1100, the triage module 1090 may use the model 1060 to determine a triage category for a patient. The determined triage category may then be presented through the interface 1100 to the operator of the triage system 1080. The triage system 1080 may reside in any desired type of computing device, such as a smartphone, a laptop, etc. Once a triage category has been determined for a patient, the appropriate action for that classification is undertaken. For example, the patient may be transported (via an ambulance 1110 or other vehicle) to a facility chosen based on the triage classification.

Devices already present in a first responder setting (e.g., on ambulances, medical helicopters, fire trucks, etc.) such patient monitors, etc. are computing devices having a processor, storage, display, etc. In one embodiment, such a device may be configured to include the triage system 1080 or a triage module 1090 in a fairly easy or straightforward manner. Therefore, a triage classification system as depicted herein may be integrated into a pre-hospital setting without additional equipment or space requirements. As a result, these types of embodiments provide desired pre-hospital triaging recommendations without a significant increase in cost or complexity.

Figure 2:
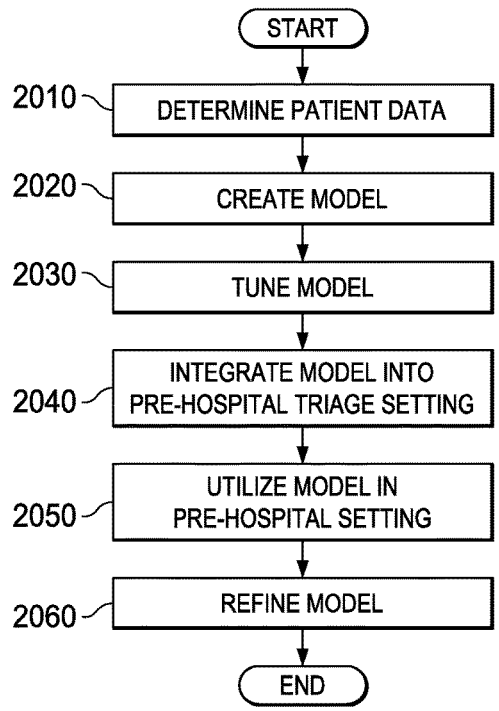
FIG. 2 is a flow diagram representing one embodiment of a method for determining a triage category.

FIG. 2 is a flow chart of one embodiment of a method for developing and deploying a triage system. Initially, at step 2010, patient data is determined. In one example, the patient data is collected in a pre-hospital setting. To develop a model, patient data is collected from a plurality of patients. In one embodiment, the patient data is collected in the same pre-hospital setting for which it is desired to implement the triage system, such that the developed triage system will be tailored to that particular pre-hospital setting. In one example, patient data is collected from patients transported to, or treated at, trauma center(s) within a geographical region which have been assigned a triage category. The collected patient data may include the triage category the patient was assigned in the pre-hospital setting, vital signs determined at multiple points in the pre-hospital environment, patient demographics, mechanism of injury, interventions (e.g., pre-hospital fluid, medications), patient management characteristics, site of injury, disposition (e.g., the accuracy of the initial triage level assigned in the pre-hospital setting, a triage level to which the patient should have been assigned, for example, based on patient outcome or treatment, etc.), or other attributes. As one skilled in the art would understand, data can be collected relating to numerous attributes (e.g., on the order of 80 or more).

Once the patient data is obtained (step 2010) a model is created at step 2020 based on the collected data. The model may include a classifier configured to input patient data and provide a recommended triage category. To construct such a classifier the collected data may be segmented into a training set (e.g., 70% of the data) and a testing set (e.g., 30% of the data). Using this data, a statistical model that includes a classifier may be created. Such a classifier may be configured to take as input one or more values for attributes, and based on the value for those attributes, determine a triage category for the patient. In some embodiments, classifiers may be able to effectively treat these attributes as functionally continuous. The classifier can therefore catch subtle differences in values of the collected attributes that may result in difference in triage categorization even though actual differences of the values in the data set may not be large.

Optionally, at step 2030, the model may be tuned. In the tuning process, a desired under triage or over triage level may be set (e.g., a percentage). Such levels may be set according to, or tailored to a variety of criteria, including geography where the system is to be deployed, a care network, etc. The tuning of a classifier may be accomplished using cost sensitization, pruning or out of bag error such that the assignment of a triage level based on the classifier may be more likely to yield the desired under triage or over triage rate.

The model, including the classifier, may then be integrated into a pre-hospital triage system and deployed in a pre-hospital setting at step 2040. Specifically, such a triage system may have an interface for accepting inputs, which may include values for patient attributes. The triage system may then use the model to determine a triage category for a patient. This triage category may then be presented through the interface to the operator of the triage system.

Once the model is integrated into the pre-hospital setting it may be utilized to obtain a triage category recommendation in a pre-hospital environment (step 2050). An operator, such a first responder or the like, caring for a patient may manually provide inputs corresponding to the patient in a pre-hospital setting (e.g., in an ambulance or medical helicopter) to the triage system. Inputs may also be obtained through the interface automatically. The inputs may comprise values for one or more of the types of attributes that were used to create the model of the triage system.

Using the inputs received through the interface, the triage system uses the model to determine a triage category for the patient. The determined triage category may then be presented through the interface to the operator of the triage system. Additionally, in some embodiments, some amount of data used in determining the triage category (e.g., percentages of decision trees corresponding to the recommended triage category) may be presented through the interface.

It will be noted here that utilizing the model, the triage system may make triage category recommendations using fewer attributes that were used to create the model. Thus, no matter the number of attributes associated with the patient data used to create the model used in the triage system, a triage category recommendation may be provided by the triage system based on values for one or more of those attributes. As additional values for attributes, or values for additional attributes are obtained, these may be provided through the interface and a new recommended triage category (which may be the same or different) determined and presented to the operator.

According to the environment in which the triage system is deployed, the operator may be required to follow to the recommendation of the triage system and transport the patient to a trauma center corresponding to the recommended category or alternatively, the operator may utilize the recommended triage category for the patient in making his own decision about which level of trauma center to transport the patient to.

Using the data obtained when utilizing the triage system with the model in the pre-hospital setting (or other patient data), the algorithm may optionally be refined or updated at step 260. In this manner, the triage category recommendations may be constantly improved or refined.

Figure 3:
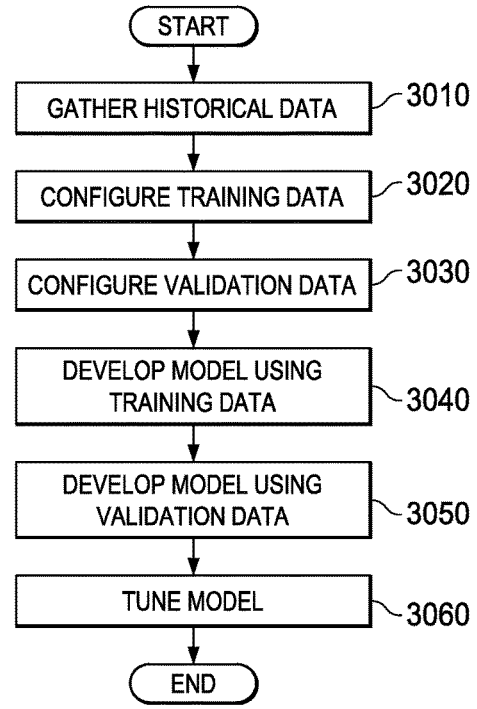
FIG. 3 is a flow chart depicting a process for developing a triage classification model.

FIG. 3 is a flow chart depicting a process for developing a triage classification model. At step 3010, historical patient data is gathered. The patient data can be gathered as new patients arrive at a facility, and/or retrieved from storage. As described above, the patient data can include any desired available data, including the triage category the patient was assigned in the pre-hospital setting, vital signs, patient demographics, mechanism of injury, interventions, patient management characteristics, site of injury, and other desired attributes.

From the gathered historical patient data, a set of training data is configured (step 3020). At step 3030, a set of validation data is configured. In one example, a certain percentage of the collected data is used as training data, and a certain percentage of the collected data is used as validation data. At step 3040, the model is developed using the training data. Each training data item includes input variables (vital signs, etc.) and an answer (the proper triage classification). In one example, a machine learning model is trained using the training data until the model is able to determine the answer (in this example, a triage classification) based on the input attributes. At step 3050, the trained model uses the validation data to test and validate the model. For example, if the model takes the inputs of the validation data and generates the correct outputs, then it can be determined that the model is adequately trained. If desired, the model can be tuned (step 3060). After the model is developed, the classifier may be tuned according to a desired over triage rate or a desired under triage rate.

FIG. 4 is a flow chart depicting a process of applying a developed triage classification model to patient data. When a patient is brought to a pre-hospital setting (e.g., a setting such as when first responders or emergency medical service personnel are assessing or transporting the patient) a patient intake process begins (step 4010). During patient intake, patient data is collected (step 4020), such as vital signs, symptoms, patient demographics, mechanism of injury, interventions, site of injury, etc. Next, the model is applied to the collected patient data (step 4030). From the input data, the model generates a triage classification score (step 4040), which, in one example, can be a number within a range of numbers. Based on desired over and under triage rates, triage guidelines, etc., the model is configured to take the triage classification score and generate a triage classification (step 4050). Once the patient has a triage classification, the health care professionals can act on the generated classification (step 4060). Actions taken in response a triage classification typically relate to transporting the patient to a health care facility that matches the triage level indicated by the model. Other actions are also possible. In the example of FIG. 4, the patient is transported to an appropriate health care facility (step 4070). Depending on the triage classification, the patient is transported to a trauma center level 1 facility (step 4080), a trauma center level 2 facility (step 4090), or a trauma center level 3 facility (step 4100). Note that while FIG. 4 shows an example with three levels of facilities, there may be more (or fewer) levels available. In addition, adult and pediatric designations may also be used.

Note that, while a model developed for one specific setting (e.g., a geographic area) can be used in other settings, although for best results, a new model can be developed for the new settings. For example, a model developed using data collected in a first city may not work as well in a second city as a model developed in the second city.

In the foregoing specification, the invention has been described with reference to specific embodiments. However, one of ordinary skill in the art appreciates that various modifications and changes can be made without departing from the scope of the invention. Accordingly, the specification and figures are to be regarded in an illustrative rather than a restrictive sense, and all such modifications are intended to be included within the scope of invention.

Although the invention has been described with respect to specific embodiments thereof, these embodiments are merely illustrative, and not restrictive of the invention. The description herein of illustrated embodiments of the invention is not intended to be exhaustive or to limit the invention to the precise forms disclosed herein (and in particular, the inclusion of any particular embodiment, feature or function is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment," "an embodiment," or "a specific embodiment" or similar terminology means that a particular feature, structure, or characteristic described in connection with the embodiment is included in at least one embodiment and may not necessarily be present in all embodiments. Thus, respective appearances of the phrases "in one embodiment," "in an embodiment," or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

Any suitable programming language can be used to implement the routines, methods or programs of embodiments of the invention described herein, including C, C++, Java, assembly language, etc. Different programming techniques can be employed such as procedural or object oriented. Any particular routine can execute on a single computer processing device or multiple computer processing devices, a single computer processor or multiple computer processors. Data may be stored in a single storage medium or distributed through multiple storage mediums, and may reside in a single database or multiple databases (or other data storage techniques). Although the steps, operations, or computations may be presented in a specific order, this order may be changed in different embodiments. In some embodiments, to the extent multiple steps are shown as sequential in this specification, some combination of such steps in alternative embodiments may be performed at the same time. The sequence of operations described herein can be interrupted, suspended, or otherwise controlled by another process, such as an operating system, kernel, etc. The routines can operate in an operating system environment or as stand-alone routines. Functions, routines, methods, steps and operations described herein can be performed in hardware, software, firmware or any combination thereof.

Embodiments described herein can be implemented in the form of control logic in software or hardware or a combination of both. The control logic may be stored in an information storage medium, such as a computer-readable medium, as a plurality of instructions adapted to direct an information processing device to perform a set of steps disclosed in the various embodiments. Based on the disclosure and teachings provided herein, a person of ordinary skill in the art will appreciate other ways and/or methods to implement the invention.

It is also within the spirit and scope of the invention to implement in software programming or of the steps, operations, methods, routines or portions thereof described herein, where such software programming or code can be stored in a computer-readable medium and can be operated on by a processor to permit a computer to perform any of the steps, operations, methods, routines or portions thereof described herein. The invention may be implemented by using software programming or code in one or more general purpose digital computers, by using application specific integrated circuits, programmable logic devices, field programmable gate arrays, optical, chemical, biological, quantum or nano-engineered systems, components and mechanisms may be used. In general, the functions of the invention can be achieved by any means as is known in the art. For example, distributed, or networked systems, components and circuits can be used. In another example, communication or transfer (or otherwise moving from one place to another) of data may be wired, wireless, or by any other means.

A "computer-readable medium" may be any medium that can contain, store, communicate, propagate, or transport the program for use by or in connection with the instruction execution system, apparatus, system or device. The computer readable medium can be, by way of example, only but not by limitation, an electronic, magnetic, optical, electromagnetic, infrared, or semiconductor system, apparatus, system, device, propagation medium, or computer memory. Such computer-readable medium shall generally be machine readable and include software programming or code that can be human readable (e.g., source code) or machine readable (e.g., object code).

A "processor" includes any, hardware system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real-time," "offline," in a "batch mode," etc. Portions of processing can be performed at different times and at different locations, by different (or the same) processing systems.

It will also be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/figures should be considered only as exemplary, and not limiting, unless otherwise specifically noted.

Furthermore, the term "or" as used herein is generally intended to mean "and/or" unless otherwise indicated. As used herein, a term preceded by "a" or "an" (and "the" when antecedent basis is "a" or "an") includes both singular and plural of such term (i.e., that the reference "a" or "an" clearly indicates only the singular or only the plural). Also, as used in the description herein, the meaning of "in" includes "in" and "on" unless the context clearly dictates otherwise.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component.

What is claimed is:

1. A method of determining patient triage categories, the method comprising:
on a triage system, developing a machine learning model that includes a classifier, the triage system having a processor and a non-transitory computer-readable medium storing instructions, the instructions when translated by the processor implementing a triage module having an interface and the machine learning model, the developing comprising:
inputting historical patient data to the triage module through the interface, the historical patient data including patient data of a plurality of patients, the patient data including attributes describing the plurality of patients in a pre-hospital setting, the attributes including triage categories assigned to the plurality of patients in the pre-hospital setting;
segmenting the historical patient data into a training set and a testing set;
constructing the classifier using the training set and the testing set, the classifier configured to take as input at least one value for the attributes and, based on the at least one value, determine a patient triage category; and
tuning the classifier according to a desired over triage rate or a desired under triage rate;
receiving, through the interface from devices in the pre-hospital setting, patient attribute data describing a patient in the pre-hospital setting;
applying the machine learning model to the collected patient attribute data to generate a triage category for the patient in the pre-hospital setting; and
presenting, through the interface, the triage category for the patient in the pre-hospital setting.

2. The method of claim 1, wherein the developing further comprises validating the machine learning model using a validation data set.

3. The method of claim 1, wherein the attributes describing the plurality of patients in the pre-hospital setting include vital signs determined at multiple points in the pre-hospital setting.

4. The method of claim 1, wherein the attributes describing the plurality of patients in the pre-hospital setting include patient demographics of the plurality of patients.

5. The method of claim 1, wherein the tuning the classifier comprises setting a desired over triage level or a desired under triage level according to at least one criteria including a geography where the triage system is to be deployed.

6. The method of claim 1, wherein the machine learning model is a statistical model.

7. The method of claim 1, wherein the classifier is an ensemble classifier.

8. A system for determining patient triage categories, the system comprising:
a computing device having a processor, a storage location, and
instructions stored on the computing device, the instructions when translated by the processor implementing a triage module comprising an interface and a computer model that includes a classifier developed by:
inputting historical patient data to the triage module through the interface, the historical patient data including patient data of a plurality of patients, the patient data including attributes describing the plurality of patients in a pre-hospital setting, the attributes including triage categories assigned to the plurality of patients in the pre-hospital setting;
segmenting the historical patient data into a training set and a testing set;
constructing the classifier using the training set and the testing set, the classifier configured to take as input at least one value for the attributes and, based on the at least one value, determine a patient triage category; and tuning the classifier according to a desired over triage rate or a desired under triage rate;

wherein the instructions when translated by the processor are further operable to perform:

receiving, through the interface from devices in the pre-hospital setting, patient attribute data describing a patient in the pre-hospital setting;

applying the computer model to the collected patient attribute data to generate a triage category for the patient in the pre-hospital setting; and presenting, through the interface, the triage category for the patient in the pre-hospital setting.

9. The system of claim 8, wherein the attributes describing the plurality of patients in the pre-hospital setting include vital signs determined at multiple points in the pre-hospital setting.

10. The system of claim 8, wherein the attributes describing the plurality of patients in the pre-hospital setting include patient demographics of the plurality of patients.

11. The system of claim 8, wherein the tuning the classifier comprises setting a desired over triage level or a desired under triage level according to at least one criteria including a geography where the system is to be deployed.

12. The system of claim 8, wherein the computer model is a statistical model.

13. The system of claim 8, wherein the classifier is an ensemble classifier.

14. The system of claim 8, wherein development of the computer model further comprises validating the computer model using a validation data set.

15. A computer program product comprising a non-transitory computer-readable medium storing instructions, the instructions when translated by a processor implements a triage module for a triage system having an interface and a computer model that includes a classifier, the computer model developed by:

inputting historical patient data to the triage module through the interface, the historical patient data including patient data of a plurality of patients, the patient data including attributes describing the plurality of patients in a pre-hospital setting, the attributes including triage categories assigned to the plurality of patients in the pre-hospital setting;

segmenting the historical patient data into a training set and a testing set;

constructing the classifier using the training set and the testing set, the classifier configured to take as input at least one value for the attributes and, based on the at least one value, determine a patient triage category; and tuning the classifier according to a desired over triage rate or a desired under triage rate;

wherein the instructions when translated by the processor are further operable to perform:

collecting, through the interface from devices in the pre-hospital setting, patient attribute data describing a patient in the pre-hospital setting;

applying the computer model to the collected patient attribute data to generate a triage category for the patient in the pre-hospital setting; and presenting, through the interface, the generated triage category for the patient in the pre-hospital setting.

16. The computer program product of claim 15, wherein the attributes describing the plurality of patients in the pre-hospital setting include vital signs determined at multiple points in the pre-hospital setting.

17. The computer program product of claim 15, wherein the attributes describing the plurality of patients in the pre-hospital setting include patient demographics of the plurality of patients.

18. The computer program product of claim 15, wherein the tuning the classifier comprises setting a desired over triage level or a desired under triage level according to at least one criteria including a geography where the system triage is to be deployed.

19. The computer program product of claim 15, wherein the computer model is a statistical model.

20. The computer program product of claim 15, wherein the classifier is an ensemble classifier.

* * * * *